United States Patent
Jussel et al.

(10) Patent No.: US 9,228,782 B2
(45) Date of Patent: Jan. 5, 2016

(54) MICROWAVE OVEN

(75) Inventors: Rudolf Jussel, Feldkirch-Gisingen (AT); Jürgen Laubersheimer, Buchs, NY (US); Christian Werling, Lindau (DE)

(73) Assignee: Ivoclar Vivadent AG, Schaan (LI)

( * ) Notice: Subject to any disclaimer, the term of this patent is extended or adjusted under 35 U.S.C. 154(b) by 931 days.

(21) Appl. No.: 13/244,968

(22) Filed: Sep. 26, 2011

(65) Prior Publication Data

US 2012/0080425 A1    Apr. 5, 2012

(30) Foreign Application Priority Data

Oct. 1, 2010 (EP) .................... 10186238

(51) Int. Cl.
*H05B 6/64* (2006.01)
*F27B 17/02* (2006.01)
*A61C 13/20* (2006.01)
*H05B 6/80* (2006.01)

(52) U.S. Cl.
CPC ............ *F27B 17/025* (2013.01); *A61C 13/203* (2013.01); *H05B 6/6491* (2013.01); *H05B 6/80* (2013.01); *H05B 2206/046* (2013.01)

(58) Field of Classification Search
CPC .... H05B 6/647; H05B 6/6482; H05B 6/6491; H05B 6/6494; H05B 6/80
USPC ........................ 219/730, 756, 759
See application file for complete search history.

(56) References Cited

U.S. PATENT DOCUMENTS

| | | | |
|---|---|---|---|
| 5,432,325 A * | 7/1995 | Katz et al. ................. | 219/759 |
| 2007/0145048 A1* | 6/2007 | Ripley ..................... | 219/759 |
| 2008/0206569 A1* | 8/2008 | Whitehead et al. ......... | 428/408 |
| 2008/0274604 A1* | 11/2008 | Sanchez et al. ............ | 438/507 |
| 2009/0079101 A1* | 3/2009 | Laubersheimer et al. .... | 264/16 |
| 2009/0302030 A1* | 12/2009 | Quantrille et al. ......... | 219/678 |
| 2010/0025395 A1 | 2/2010 | Laubersheimer | |

FOREIGN PATENT DOCUMENTS

| | | |
|---|---|---|
| DE | 2021901 A1 | 11/1970 |
| DE | 3703163 A1 | 8/1987 |
| EP | 1060713 B1 | 12/2005 |
| EP | 2150092 A2 | 2/2010 |
| JP | 11106283 A | 4/1999 |
| WO | 2009/039220 A1 | 3/2009 |

OTHER PUBLICATIONS

Wikipedia, Broadband; http:/en.wikipedia.org/wiki/Broadband;Dec. 10, 2014;pp. 1-3.

* cited by examiner

*Primary Examiner* — Dana Ross
*Assistant Examiner* — Brandon Harvey
(74) *Attorney, Agent, or Firm* — Ann M. Knab; Thad McMurray

(57) ABSTRACT

The invention concerns a microwave oven (10) for the heat treatment of ceramic components, in particular of dental ceramic components (12). It is equipped with a susceptor (14) which is positioned in the swell or in the area between a source of microwaves and the component. The susceptor (14) is made of highly pure silicon carbide of hexagonal, rhombohedral or cubic crystal structure, which has in particular a 2H, 4H, 6H or 3C crystal structure.

20 Claims, 2 Drawing Sheets

MICROWAVE OVEN

CROSS-REFERENCE TO RELATED APPLICATIONS

This application claims the benefit of European Patent Application No. 10 186 238.1 filed Oct. 1, 2010, which is hereby incorporated by reference in its entirety.

TECHNICAL FIELD

The invention relates to a microwave oven for the heat treatment of substances and/or components, more specifically for the heat treatment of ceramics, and even more specifically, for the heat treatment of dental ceramic components.

BACKGROUND OF THE INVENTION

Microwave ovens for the production of substances and/or components, in particular ceramic components and/or dental ceramics have been known for some time. Reference is made, by way of example, to EP 1 060 713 A2. Also the use of susceptors for microwaves has been known for a long time, for instance from DE-OS 2 021 901, which mentions the use of susceptors as well as heating via microwaves.

Different materials which can be used for microwave heating devices are mentioned in DE 37 03 163 A1 and corresponding U.S. Pat. Nos. 4,800,247 and 5,057,659, which US patents are hereby incorporated by reference. The susceptor mentioned therein serves for absorbing microwave radiation.

In the heat treatment of dental ceramics with the help of microwaves, it is essential for the susceptors used to provide coupling over a wide area. This requirement can be fulfilled comparatively well with the help of silicon carbide which, moreover, has a thermal stability of >2000° C., and therefore securely covers the temperature range desired for the heat treatment of ceramics, in particular of dental ceramics.

The silicon carbide qualities used so far, however, often have impurities resulting from the production process, for instance of vanadium or manganese etc., which may, for example, lead to discolorations of the objects to be heat-treated.

In particular with large ceramic components and/or multi-member dental bridges or larger dental replacement parts, it is essential for the heat to be spread uniformly and therefore for heat-induced stresses and the resulting possible formation of microfissures to be avoided in the objects to be heat-treated.

SUMMARY

The invention provides a microwave oven for the heat treatment of substances and components, in particular, ceramic components, in particular for the heat treatment of dental ceramic components, having good cycle time, without running the risk of compromising quality in the finished dental restoration part.

It has been recognized that amazingly the coupling behaviour of SiC single crystals is extraordinarily better than that of susceptors of commercially available SiC qualities commonly used so far. This extraordinarily better coupling behaviour comes with extraordinary thermal conductivity which supports the temperature compensation among any substances and/or components to be heat-treated and inserted into the oven space, independently of their own coupling behaviour.

In contrast to this, the SiC qualities described in this invention are highly pure due to the fact that they consist only of one crystal of Si and C. In particular, these have impurities of less than $10^{-1}$, preferably of less than $20^{-2}$ ppm.

Compared with commercially available silicon carbide components, thermal conductivity is significantly better, which makes it possible that the heating gradients can be increased considerably, for instance also with components of complex geometry, to heating rates of more than 400° K/minute. Apparently, the highly pure silicon carbide, which is preferably used as single crystal, distributes the heat introduced considerably better, such that there is no more inhomogeneous heat distribution.

In particular, with components which do not have a good thermal conductivity and/or auto-coupling to the microwave radiation, the use of the SiC single crystal described as a susceptor is advantageous since this crystal itself couples excellently to the microwave radiation and the resulting heat is spread in a very homogeneous fashion in an extremely short time. Thanks to these properties, it is possible to reduce potential dwell times necessary in conventional ovens and/or heat more quickly due to the rapid homogenisation of temperature, which results in considerably reduced process durations. Using an SiC single crystal, this can all be done without running the risk of thermal stresses or microfissures, so the heat treatments of substances and/or components can be done in a shorter time, with at least equal, possibly better quality than with the conventional technology.

Surprisingly, the risk of intrinsic defects and also discolorations is extremely reduced. Since the SiC basic material consists of one crystal of silicon and carbon which are deposited out of the basic phase at a SiC core crystal as a result of a sublimation process, no possibilities arise for impurities to be caused in the substance and/or the component to be heat-treated, in particular in the dental ceramic component, such that there is not really a risk of discolorations either.

Surprisingly, a distinctly lower mass can be used for the susceptor compared with SiC qualities used so far, which entails a considerably better relation between heating output and susceptor mass.

Surprisingly, the use of highly pure silicon carbide of hexagonal or cubic crystal structure for a susceptor—basically almost independently of the outer shape of the susceptor—results in an improved coupling of the substance and/or the ceramic part to be heated. The susceptor couples in a very homogeneous fashion over a very wide range of temperatures and immediately forwards the heat absorbed to the substance or the dental ceramic component to be heat-treated due to its extraordinary thermal conductivity.

For instance, the susceptor can have a cup-shaped basic structure, such that the dental restoration part is surrounded by the susceptor on all sides horizontally and is uniformly exposed to heat.

In accordance with the present invention, it is furthermore favourable that also a one-sided exposure of, for example a pot-shaped, susceptor to microwave radiation will not lead to the creation of important temperature gradients. As a result of the high thermal conductivity, also the part of the susceptor pointing away from the microwave source will be heated immediately, and the problem of possible thermal stresses and the microfissures resulting from that, even in connection with faster heating, will be reduced.

This surprising feature leads to the fact that the designer of the microwave oven has more creative liberties, whereas with classic susceptors, the reflection of the microwave radiation into the space of the microwave oven had to be precisely planned in order to make sure that the exposure of the susceptor to microwave radiation was as uniform as possible. This does not hold true any longer. Both in mono-mode and in multi-mode operation, the desired uniformity of temperature as well as a robust adaptation of the (oven) equipment can be provided without any problem.

In an advantageous embodiment, the crystal susceptor has a smooth and optically attractive surface. In contrast to micro-dot contact, such as it arises for example with sintered silicon carbide bodies, this also has the particular advantage that a large-surface contact is possible, which improves the heat-transition resistance between the susceptor and the dental restoration part.

It is to be understood that the shape of the crystal susceptor or susceptors in accordance with the present invention can be largely adapted to the requirements. For instance, it is also possible to provide susceptor bodies which are arranged, each individually, in extremely dense spherical packing, are shaped as crystal susceptors, and surround the object to be heat-treated in such a fashion that they are in close contact with it.

In accordance with the present invention, it is especially favourable that for the heat treatment of substances and/or components, in particular of ceramic components, particularly of dental ceramic components, with the help of a susceptor positioned in the swell or in the area between a source of microwaves and the component, which area is exposed to microwave radiation, that the susceptor is made of highly pure silicon carbide of hexagonal, rhombohedral or cubic crystal structure, in particular of 2H, 4H, 6H or 3C crystal structure.

In accordance with a favourable embodiment, it is intended that the silicon carbide is a single crystal.

In accordance with a favourable embodiment, it is intended that the component be coupled to microwave radiation in a broad-band fashion, in particular via a band of more than 10% of the fundamental microwave frequency of the source of microwaves used, in particular already at room temperature and/or at 0° C. and also at the maximum temperature used for sintering dental ceramics, in particular also at 2000° C.

In accordance with a favourable embodiment, it is intended that the microwave oven has a cavity suited for mono-mode or for multi-mode operation.

In accordance with a favourable embodiment, it is intended that the susceptor is formed in such a fashion that it is inert or non-reactive towards the substance and/or the ceramic component, in particular at its surface, and in case of contact, a chemical reaction between component and susceptor is avoided even at high temperatures.

In accordance with a favourable embodiment, it is intended that the susceptor has a thermal conductivity of greater than about 200 W/mK, in particular of approximately about 350 W/mK.

In accordance with a favourable embodiment, it is intended that the susceptor has a geometrical configuration in ring-, disc- or other geometrical shapes and is in immediate contact with or in immediate proximity of the component and/or substance to be heat-treated.

In accordance with a favourable embodiment, it is intended that a maximum distance between the susceptor and the substance or component is less than about 5 cm.

In accordance with a favourable embodiment, it is intended that the microwave oven has a closed interior, which is in wave connection with the source of microwaves, with the source of microwaves being the only heat source.

In accordance with a favourable embodiment, it is intended that the microwave oven has an additional heat source, in particular a heat source radiating in the infrared spectrum, which exposes the susceptor and/or the component or the substance to thermal energy.

In accordance with a favourable embodiment, it is intended that an optical temperature measuring sensor is directed to a surface of the susceptor, in particular to a surface of the susceptor which is pointing in the direction towards the component, if an open susceptor is employed, and registers the temperature of the component based on the surface of the susceptor.

In accordance with a favourable embodiment, it is intended that the substance or the component is not self-coupling for microwave radiation and is heated up entirely by the heat emission of the susceptor.

In accordance with a favourable embodiment, it is intended that the substance or the component is independently coupling for microwave radiation and the susceptor is shaped as a base-load microwave sink and absorbs a previously determined load of microwave radiation and in particular causes a uniform distribution of temperature, free of hot spots.

In accordance with a favourable embodiment, it is intended that the interior of the microwave oven is closed in such a fashion that it is gas-tight and over- or under-pressure can be set, and in particular can be washed with the help of a flush gas and is particularly preferably shaped as an open or closed continuous or tunnel furnace.

In accordance with a favourable embodiment, it is intended that the susceptor prevents and shields the coupling of the ceramic components to the electromagnetic radiation and in particular permits through to the component less than 10% of the arriving electromagnetic radiation.

In accordance with a favourable embodiment, it is intended that the susceptor has a smooth and optically attractive surface.

BRIEF DESCRIPTION OF THE DRAWINGS

Embodiments of the present invention will be more fully understood and appreciated by the following Detailed Description in conjunction with the accompanying drawings, in which.

DETAILED DESCRIPTION

Figure 1:
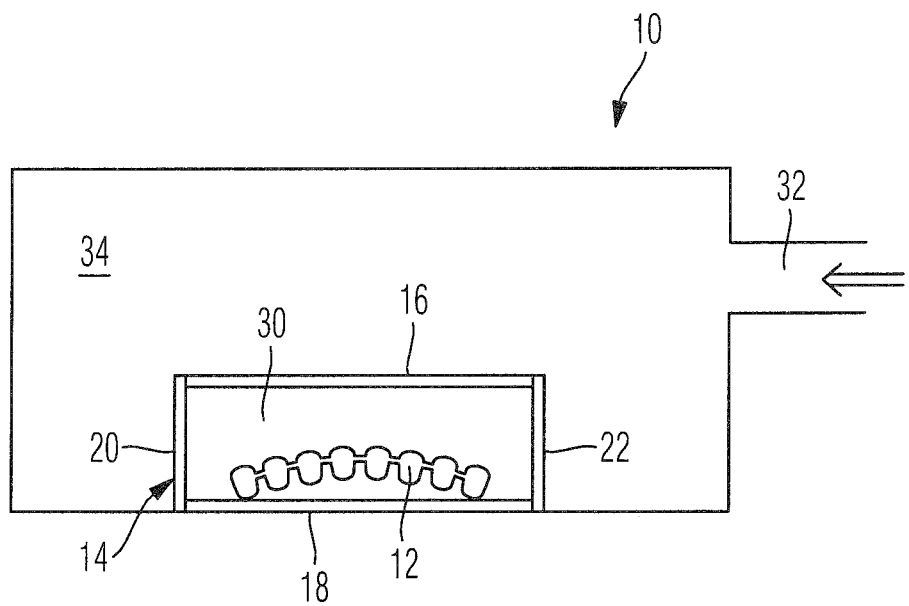
FIG. 1 is a schematic view of a microwave oven in one possible embodiment of the invention.

FIG. 1 shows a schematic depiction of a microwave oven 10 for the heat treatment of a dental ceramic component 12. As can be seen, the dental ceramic component is complex and large and is shown here by way of example. It is to be understood that instead of this, any other suitable dental ceramic components can be heat-treated, for instance also a number of components together.

In accordance with the present invention, a special susceptor 14 is to be provided, which surrounds the component 12 at least partially. In the exemplary embodiment shown, it surrounds it completely.

The susceptor 14 in accordance with the present invention is a susceptor made of highly pure silicon carbide of hexagonal crystal structure, with a 4H crystal structure being intended by way of example.

It is to be understood that instead of this, it is possible without any problem to provide a 2H or a 6H crystal structure, or a cubic 3C crystal structure.

Preferably, the susceptor 14 is a single crystal as far as the individual walls, including the bottom and top walls, are concerned, respectively.

Figure 2:
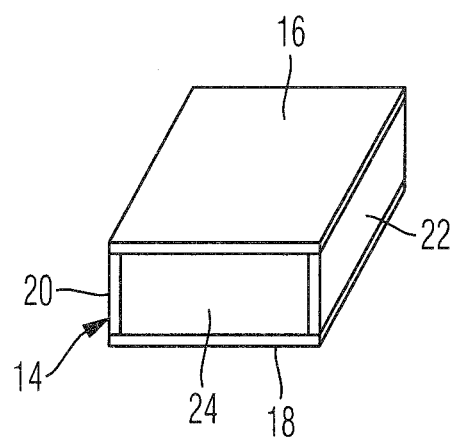
FIG. 2 is a schematic view of the susceptor produced in accordance with the present invention in the embodiment of FIG. 1.

The susceptor 14, which is also depicted in a perspective view in FIG. 2, consists of individual plate-shaped walls for production-process reasons. When designing the susceptor, the thickness of the walls can be kept very low. It is to be understood that the thickness of the walls can be adapted to the requirements in any fashion desired.

In the exemplary embodiment depicted, the susceptor 14 has a rectangular or cylindrical shape and is closed. It has a top wall 16, a bottom wall 18, a left side wall 20, a right side wall 22, a front side wall 24 as well as a back wall which is not visible.

Instead of this, an open construction without the top wall 16 is also possible.

The walls, with the exception of the top wall 16, are connected with each other in any suitable fashion desired, for instance with the help of grooves sunk in. The top wall 16, in contrast, is simply placed on top and, if needed, has a slight chamfer at the end portion, which makes it sink a little into the interior 30 of the susceptor, such that it is captively in contact with the side walls 20, 22, the front wall 24 and the back wall.

All walls 16 to 24 are cut out of one plate which is produced as a single crystal. For the production, poly-crystalline SiC is preferably sublimed. The PVT process can be used, or the modified Lely method, or any other suitable process for producing single-crystal silicon carbide. It is also possible to produce the single crystal with the help of Chemical Vapor Deposition in an epitaxial fashion. One possible process is described in WO 01/04389.

It is to be understood that any other forms of production of an at least partially closed susceptor 14 can be put into practice. For a realization with the help of single crystals, however, the use of plane walls is of advantage.

As can be seen, a rather low thickness of the walls is intended for the design of the susceptor 14. The thickness of the walls can be reduced to distinctly less than 3 mm, depending on the size of the susceptor 14.

Whereas a hexagonal crystal structure is preferably used, of which more than 170 modifications are known with SiC, it is also possible to use the cubic crystal structure or zinc-blende structure, in which the crystal is made up of two cubic, face-centered grids of different types of atoms, which are displaced with respect to each other by a quarter of the spatial diagonal. This SiC is also referred to as $\beta$-SiC, whereas the other SiC modifications have either a hexagonal or a rhombohedral unit cell and are collectively referred to as $\alpha$-SiC. Alpha-phases only occur to an important extent in the creation with the help of temperatures of more than 1800° C., i.e., for example, in sublimation breeding at 2000° C., as is intended in accordance with WO 01/04389 to which full reference is herein made.

In a basically known fashion, the microwave oven 10 is supplied with microwave energy via a magnetron which is not depicted, the energy being supplied to the interior 34 of the microwave oven 10 via an entrance 32. The interior 34 is considerably larger than the susceptor 14, for instance in a volume ratio of 20:1. Even if mode stirrers can be provided, this is not necessary in accordance with the present invention, for despite the low thickness of walls, the thermal conductivities provided of 350 W/mK or even 400 W/mK with $\alpha$-SiC and also with $\beta$-SiC are excellent, such that the microwave energy introduced at a possible "hot spot" is distributed quickly.

Due to the low thickness of the walls, the SiC, on the other hand, has a particularly low heat capacity, which supports a fast heating-up.

Figure 3:
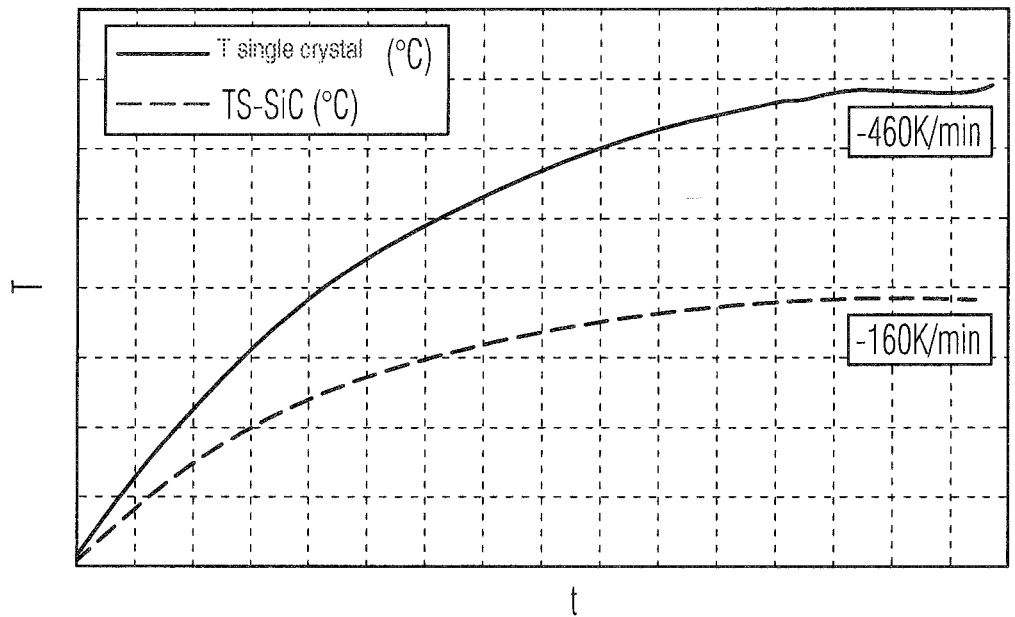
FIG. 3 is a diagram for the comparison of the heating-up curve of a microwave oven in accordance with the present invention in the embodiment of FIG. 1.

In accordance with FIG. 3, a heating-up curve of a microwave oven 10 in accordance with the present invention is depicted by a solid line, whereas the heating-up curve of a conventional microwave oven is depicted by a broken line. The heating-up is done, in accordance with the present invention, with a maximum lateral sway of 360 Kelvin/min, whereas a commonly used microwave oven 10 reaches a maximum of 180 Kelvin/min.

Figure 4:
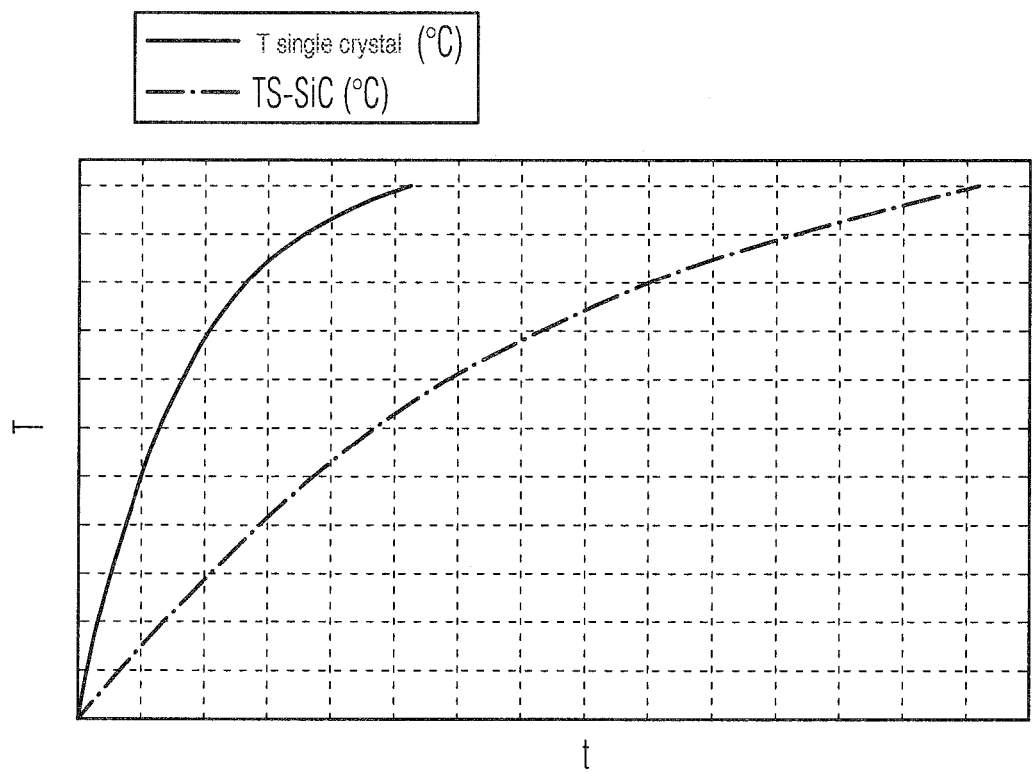
FIG. 4 is another heating-up curve of the microwave oven in accordance with the present invention in comparison with a conventionally available SiC-driven microwave oven.

In FIG. 4, a modified heating-up curve for an oven of lower heat capacity and accordingly lower cycle time is depicted. Here as well, it is visible from the comparison between the solid line of the microwave oven in accordance with the present invention and the broken line of the commonly used microwave oven that the heating-up gradient in accordance with the present invention is clearly improved.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. Microwave oven for the heat treatment of one or more components, comprising
   a susceptor, positioned in a swell or in an area between a source of microwaves and the one or more components, which area is exposed to microwave radiation,
   wherein the susceptor is made of highly pure silicon carbide of hexagonal, rhombohedral or cubic crystal structure,
   wherein the silicon carbide is a single crystal in the form of a plate, and
   wherein all walls of the susceptor are cut out of the plate.

2. Microwave in accordance with claim 1, wherein the one or more components comprise ceramic materials.

3. Microwave in accordance with claim 2, wherein the ceramic materials comprise dental ceramic materials.

4. Microwave oven in accordance with claim 1, wherein the crystal structure comprises 2H, 4H, 6H or 3C crystal structure.

5. Microwave oven in accordance with claim 1, wherein the one or more components is coupled to microwave radiation in a broad-band fashion.

6. Microwave oven in accordance with claim 5, wherein the broad-band fashion is a band of more than 10% of the fundamental microwave frequency of the source of microwaves used already at room temperature and/or at 0° C. and also at the maximum temperature used for sintering dental ceramics, also at 2000° C.

7. Microwave oven in accordance with claim 1, wherein the microwave oven has a cavity suited for mono-mode or for multi-mode operation.

8. Microwave oven in accordance with claim 1, wherein the susceptor is formed in such a fashion that it is inert or non-reactive towards the one or more components, at its surface, and in case of contact, a chemical reaction between component and susceptor is avoided even at high temperatures.

9. Microwave oven in accordance with claim 1, wherein the susceptor has a thermal conductivity of greater than about 200 W/mK.

10. Microwave oven in accordance with claim 1, wherein the susceptor has a thermal conductivity of about 350 W/mK.

11. Microwave oven in accordance with claim 1, wherein the susceptor has a geometrical configuration of ring-, disc- or other geometrical shapes and is in immediate contact with or in immediate proximity of the component and/or substance to be heat-treated.

12. Microwave oven in accordance with claim 1, wherein a maximum distance between the susceptor and the substance or component is less than about 5 cm.

13. Microwave oven in accordance with claim 1, wherein the microwave oven has a closed interior, which is in wave connection with the source of microwaves, with the source of microwaves being the only heat source.

14. Microwave oven in accordance with claim 1, wherein the microwave oven has an additional heat source radiating in the infrared spectrum, which exposes the susceptor and/or the one or more components to thermal energy.

15. Microwave oven in accordance with claim 1, wherein an optical temperature measuring sensor is directed to a surface of the susceptor which is pointing in the direction towards the one or more components, and registers the temperature of the component based on the surface of the susceptor.

16. Microwave oven in accordance with claim 1, wherein the one or more components is not self-coupling for microwave radiation and is heated up entirely by the heat emission of the susceptor.

17. Microwave oven in accordance with claim 1, wherein the one or more components is independently coupling for microwave radiation and the susceptor is shaped as a base load microwave sink and absorbs a previously determined load of microwave radiation and causes a uniform distribution of temperature, free of hot spots.

18. Microwave oven in accordance with claim 1, wherein an interior of the microwave oven is closed in such a fashion that it is gas-tight and over- or under-pressure can be set.

19. Microwave oven in accordance with claim 1, wherein an interior can be washed with the help of a flush gas and is shaped as an open or closed continuous or tunnel furnace.

20. Susceptor for a microwave oven, wherein the susceptor is made of highly pure silicon carbide of hexagonal, rhombohedral or cubic crystal structure, wherein the silicon carbide is a single crystal in the form of a plate, and wherein all walls of the susceptor are cut out of the plate.

* * * * *